(12) United States Patent
Liu et al.

(10) Patent No.: US 9,766,193 B2
(45) Date of Patent: Sep. 19, 2017

(54) LIQUID CONCENTRATION DETECTING DEVICE

(71) Applicants: Industrial Technology Research Institute, Hsinchu (TW); Etian Technology Ltd., New Taipei (TW)

(72) Inventors: Tzu-Yu Liu, Taichung (TW); Kuo-Chuang Chiu, Hsinchu (TW); Hung Tien, New Taipei (TW); Shiou-Lan Hu, New Taipei (TW); Yeh-Chyang Huang, New Taipei (TW)

(73) Assignees: Industrial Technology Research Institute, Hsinchu (TW); QIAN JUN TECHNOLOGY LTD., New Taipei (TW)

( * ) Notice: Subject to any disclaimer, the term of this patent is extended or adjusted under 35 U.S.C. 154(b) by 339 days.

(21) Appl. No.: 14/583,212

(22) Filed: Dec. 26, 2014

(65) Prior Publication Data

US 2016/0084780 A1     Mar. 24, 2016

(30) Foreign Application Priority Data

Sep. 18, 2014   (TW) .............................. 103132249 A (51) Int. Cl.
    *G01N 25/00*          (2006.01)
    *G01N 25/18*          (2006.01)
    *F01N 3/20*           (2006.01)

(52) U.S. Cl.
    CPC ............ *G01N 25/00* (2013.01); *F01N 3/2066* (2013.01); *G01N 25/18* (2013.01);
(Continued)

(58) Field of Classification Search
    CPC ........ G01N 25/62; G01N 25/64; G01N 19/10; G01N 33/18; G01N 33/2823;
(Continued)

(56) References Cited

U.S. PATENT DOCUMENTS 7,829,024 B2    11/2010   Izutani et al.
8,578,761 B2 *   11/2013   Fukumura ............ G01N 27/226
                                                                        73/61.41

(Continued)

FOREIGN PATENT DOCUMENTS

CN        1892208        1/2007
CN      101042359        9/2007

(Continued)

OTHER PUBLICATIONS

"Notice of Allowance of Taiwan Counterpart Application," issued on Sep. 17, 2015, p. 1-p. 5.

*Primary Examiner* — John Fitzgerald
*Assistant Examiner* — Truong Phan
(74) *Attorney, Agent, or Firm* — Jianq Chyun IP Office (57) ABSTRACT

A liquid concentration detecting device including a first substrate, a first temperature sensing element and a concentration sensor is provided. The first temperature sensing element and the concentration sensor are respectively disposed on opposite first surface and second surface of the first substrate. The concentration sensor includes a second substrate, a porous element, a heating element and a second temperature sensing element. The second substrate is disposed above the second surface. A portion of the liquid flows into the concentration sensor through the porous element, and the heating element heats the liquid in the concentration sensor. The second temperature sensing element measures the temperature variation of the liquid in the concentration sensor. The measured temperature and the temperature variation are compared to deduce a concentration of the liquid under detection.

20 Claims, 5 Drawing Sheets

(52) U.S. Cl.
CPC .... *F01N 2610/02* (2013.01); *F01N 2610/148* (2013.01); *F01N 2900/1818* (2013.01)

(58) Field of Classification Search
CPC .. G01N 29/024; G01N 33/04; G01N 33/2835; G01N 27/18; G01N 33/1833; G01N 25/08; G01N 25/00; G01N 25/04; G01N 27/06; G01N 25/18; F02D 41/1441; F02D 41/1497; F01N 11/007; F01N 2550/02; F01N 3/2066; F01N 2900/1818; F01N 2610/02; F01N 2610/148; F02P 5/1506; F02P 5/152; B01J 19/0046; B01J 35/0006; B01J 2219/00283
USPC ................... 73/61.41, 61.46, 61.76, 335.06; 422/82.12; 123/406.12; 60/276
See application file for complete search history.

(56) References Cited

U.S. PATENT DOCUMENTS

| | | |
|---|---|---|
| 2001/0000852 A1 | 5/2001 | Mauze et al. |
| 2006/0026949 A1 | 2/2006 | Takahata et al. |
| 2006/0243248 A1 | 11/2006 | Kawanishi et al. |
| 2010/0319436 A1 | 12/2010 | Sun et al. |

FOREIGN PATENT DOCUMENTS

| | | |
|---|---|---|
| CN | 103354888 | 10/2013 |
| EP | 1538437 | 6/2005 |

\* cited by examiner

LIQUID CONCENTRATION DETECTING DEVICE

CROSS-REFERENCE TO RELATED APPLICATION

This application claims the priority benefit of Taiwan application serial no. 103132249, filed on Sep. 18, 2014. The entirety of the above-mentioned patent application is hereby incorporated by reference herein and made a part of specification.

TECHNICAL FIELD

The disclosure relates to a liquid concentration detecting device.

BACKGROUND

Along with developments and applications of technologies, liquid concentration detecting devices are needed in various fields, such as etchant formulation in a wafer manufacturing process or vehicle emission in an environment protection field.

Taking the vehicle emission for example, in order to comply with an environmental emission standard, heavy-duty diesel vehicles internationally tend to adopt a selective catalytic reduction (SCR) technique to reduce emissions of nitrogen oxide (NOx) in the exhaust. In detail, an SCR system includes vehicle urea and a SCR device. The vehicle urea is injected into the combusted waste gas from a urea tank and decomposes into ammonia ($NH_3$), such that a chemical reduction occurs to NOx by $NH_3$ in the SCR device to transform the NOx into Nitrogen and water which cause no influence to the natural environment. Accordingly, the SCR system needs to consume a reactant (i.e., the vehicle urea) for normal operation. A car urea solution is a solution of 32.5% urea in water, where the concentration of the urea solution is strictly restricted, otherwise the NOx emission of a car will exceed the standard and the SCR system of a car may also be damaged.

SUMMARY

The disclosure introduces a liquid concentration detecting device adapted for detecting a concentration of a liquid and capable of obtaining an accurate measured result.

According to an embodiment of the disclosure, a liquid concentration detecting device adapted for detecting a concentration of a liquid is introduced. The liquid concentration detecting device includes a first substrate, a first temperature sensing element and a concentration sensor. The first substrate has a first surface and a second surface opposite to each other, and the first temperature sensing element is disposed on the first surface. The first temperature sensing element measures the temperature of the liquid in the external of the liquid concentration detecting device. The concentration sensor is disposed on the second surface of the first substrate. The concentration sensor includes a second substrate, a porous element, a heating element and a second temperature sensing element. The second substrate is disposed on the second surface of the first substrate and has a third surface and a fourth surface opposite to each other. The third surface of the second substrate faces the second surface of the first substrate. The porous element is located above the fourth surface of the second substrate, and a portion of the liquid flows into the concentration sensor through the porous element. The heating element heats the portion of the liquid flowing into the concentration sensor. The second temperature sensing element measures the temperature variation of the portion of the liquid flowing into the concentration sensor. The measured temperature and temperature variation are compared to obtain the concentration of the liquid under detection.

Several exemplary embodiments accompanied with figures are described in detail below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The term "coupling/coupled" used in this specification (including claims) may refer to any direct or indirect connection means. For example, "a first device is coupled to a second device" should be interpreted as "the first device is directly connected to the second device" or "the first device is indirectly connected to the second device through other devices or connection means." Moreover, wherever appropriate in the drawings and embodiments, elements/components/steps with the same reference numerals represent the same or similar parts. Elements/components/steps with the same reference numerals or names in different embodiments may be cross-referenced.

Terminologies used in the disclosure such as "first" and "second" used to describe each element, component, location, layer or section etc. should not be construed as limiting these elements, components, locations, layers or sections. These terminologies are merely used to differentiate between one element, component, location, layer or section, and another element, component, location, layer or section. Therefore, without departing from the teachings of the embodiments, the first element, component, location, layer or section referred in the disclosure below may also be referred as the second element, component, location, layer or section.

To facilitate description, Spatially relative terms, such as "beneath", "below", "lower", "under", "above," "upper," "over" and the like, may be used herein for ease of description to describe one element or structural feature's relationship to another element(s) or structural feature(s) as illustrated in the drawings. It will be understood that the spatially relative terms are intended to encompass different orientations of the device in use or operation in addition to the orientation depicted in the drawings. For example, if the device in the drawings is turned over, elements described as "below" or "beneath" or "under" other elements or structural features would then be oriented "above" or "over" the other elements or structural features. Thus, the exemplary terms "below" and "under" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated structural features, integers, steps, operations, elements, and/or components, but do not preclude the presence or addition of one or more other structural features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. Therefore, the regions illustrated in the figures are schematic in nature and their shapes are not intended to illustrate the actual shape of a region of a device and are not intended to limit the scope of example embodiments.

Unless otherwise defined, all terms (including technical and scientific teens) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

The disclosure introduces a liquid concentration detecting device adapted for detecting a concentration of a liquid. The liquid concentration detecting device includes a first substrate, a first temperature sensing element and a concentration sensor. The first substrate has a first surface and a second surface opposite to each other. The first temperature sensing element is disposed on the first surface of the first substrate and measures the temperature of the liquid in the external of the liquid concentration detecting device. The concentration sensor is disposed on the second surface of the first substrate and includes a second substrate, a porous element, a heating element and a second temperature sensing element. The second substrate is disposed on the second surface of the first substrate and has a third surface and a fourth surface opposite to each other. The third surface of the second substrate faces the second surface of the first substrate. The porous element is located above the fourth surface of the second substrate, and a portion of the liquid flows into the concentration sensor through the porous element. The heating element heats the portion of the liquid flowing into the concentration sensor. The second temperature sensing element measures the temperature variation of the portion of the liquid flowing into the concentration sensor. The measured temperature and temperature variation are compared to obtain the concentration of the liquid under detection.

The disclosure aims at introducing a liquid concentration detecting device for detecting a concentration of a liquid, and the liquid concentration detecting device may be applied in an SCR system, to detect a concentration of a car urea solution. Furthermore, a porous element is disposed in the liquid concentration detecting device, and the porous element provides a rough surface. Thereby, the possibility of bubble attachment may be reduced to mitigate signal interference, and the liquid concentration detecting device may obtain accurate measurement results. A plurality of embodiments of the disclosure will be illustrated as follows.

[First Embodiment]

Figure 1:
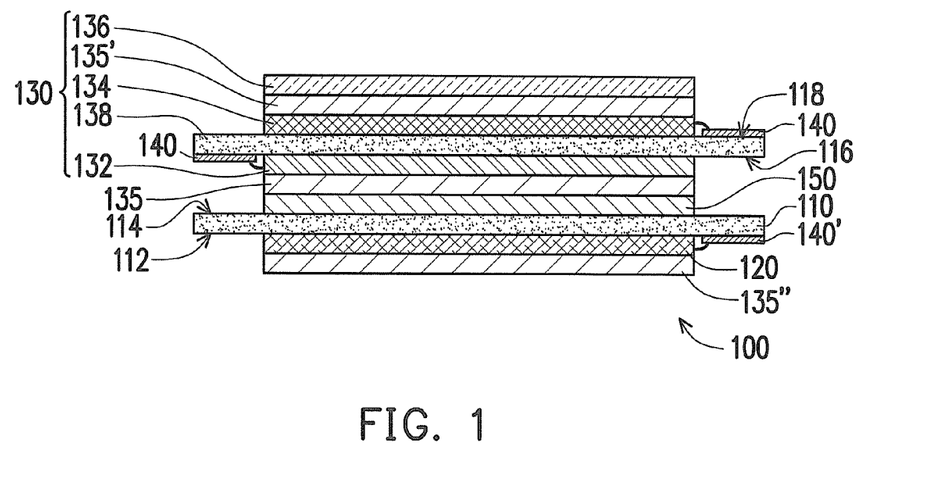
FIG. 1 is a schematic diagram illustrating a liquid concentration detecting device according to a first embodiment of the disclosure.

FIG. 1 is a schematic diagram illustrating a liquid concentration detecting device according to a first embodiment of the disclosure. With reference to FIG. 1, a liquid concentration detecting device 100 includes a first substrate 110, a first temperature sensing element 120 and a concentration sensor 130. The first substrate 110 has a first surface 112 and a second surface 114 opposite to each other, and the first temperature sensing element 120 is disposed on the first surface 112. The concentration sensor 130 is disposed on the second surface 114 of the first substrate 110. The concentration sensor 130 and the first temperature sensing element 120 are electrically independent from each other, but electrically connected with the same signal process center (not shown) in common, so as to transfer results obtained respectively back to the signal process center to process. The concentration sensor 130 includes a heating element 132, a second temperature sensing element 134, a porous element 136 and a second substrate 138. The heating element 132 is disposed on the second surface 114, and the second substrate 138 is disposed above the heating element 132. The second substrate 138 has a third surface 116 and a fourth surface 118, the heating element 132 is disposed between the second surface 114 of the first substrate 110 and the third surface 116 of the second substrate 138, the second temperature sensing element 134 is located on the fourth surface 118 of the second substrate 138, and the porous element 136 is located on the second temperature sensing element 134.

To prevent heat from being conducted to the first temperature sensing element 120 through the first substrate 110 to affect measurement results when the heating element 132 is heated, a thermal insulation layer 150 may be disposed between the first substrate 110 and the heating element 132.

In the present embodiment, the thermal insulation layer 150 is disposed on the second surface 114 of the first substrate 110. The thermal insulation layer 150 may be formed by coating a thermal insulation glue on the substrate, or may be placed on the second surface 114 of the first substrate 110 after forming a layer in sheet form by using a thermal insulation material, in which the forming of the thermal insulation layer 150 is not limited thereto. The thermal insulation layer 150 may be formed by selecting various materials with a thermal insulation nature.

At least one sealing layer may be further disposed in the liquid concentration detecting device 100 according to actual requirements, so as to improve overall structural strength of the liquid concentration detecting device 100. In the present embodiment, three sealing layers are disposed, which are a first sealing layer 135, a second sealing layer 135', and a third sealing layer 135", respectively. In detail, the first sealing layer 135 is disposed between the heating element 132 and the thermal insulation layer 150, the second sealing layer 135' is disposed between the second temperature sensing element 134 and the porous element 136, and the third sealing layer 135" is disposed on a surface of the first temperature sensing element 120 which is relative far away from the first surface 112 of the first substrate 110.

It is to be additionally mentioned that the positions of the sealing layers 135, 135' and 135" provide not only an effect of insulating the two stacking elements from each other (e.g., the first sealing layer 135 is disposed between the concentration sensor 130 and first substrate 110 to electrically insulate the concentration sensor 130 from the first substrate 110), but also an effect of protecting element surfaces (e.g., the third sealing layer 135" disposed on the surface of the first temperature sensing element and the second sealing layer 135' disposed between the second temperature sensing element 134 and the porous element 136). The second sealing layer 135' may further provide the second temperature sensing element 134 with waterproof protection, so as to prevent the absorbed water in the porous element 136 from polluting the second temperature sensing element 134.

It should be mentioned that the persons of the art may further optionally omit the first sealing layer 135 from the disposition in accordance with demands in case the liquid concentration detecting device 100 has sufficient overall strength, and the stacking elements are capable of being prevented from electrically connecting with each other by means of circuit configuration. For example, in case a circuit of one of the two stacking elements is gathered at the left side, while a circuit of the other is gathered at the right side, the two elements may achieve electrically insulating from each other by means of the locally dense circuit configuration when the two elements are stacked together. In addition, the sealing layers 135, 135' and 135" may be made of a glass material, but the disclosure is not limited thereto, and the persons may select any other material based on actual requirement for liquid concentration detecting device 100.

In the embodiment illustrated in FIG. 1, the porous element 136 is a single-layer structure made of a ceramic material, covers the second sealing layer 135'. The porous element 136 has a plurality of holes (not shown) penetrating through surfaces, where the holes are not connected with one another but penetrate through the upper and lower surfaces of the porous element or may be arranged alternately with one another and present in a form like sponge holes, and the water absorption of the porous element 136 is greater than 15%. The water absorption of the porous element 136 herein is calculated by the following equation: a weight of the water-soaked porous element 136 boiled in water minus a weight of the dry porous element 136 after being dried divided by the weight of the dry porous element 136 after being dried.

In accordance with the above, the first substrate 110 and the second substrate 138 may be ceramic substrates which have a characteristic of high thermal conductivity. The characteristic of high thermal conductivity herein refers to thermal conductivity coefficients of the first substrate 110 and second substrate 138 being greater than 20 W/M*K. For example, a high thermal-conductive ceramic substrate containing aluminum oxide has a thermal conductivity coefficient ranging from 20 W/M*K to 40 W/M*K, and a high thermal-conductive ceramic substrate containing aluminum nitride has an even higher thermal conductivity coefficient about 220 W/M*K. Additionally, the first temperature sensing element 120 and the second temperature sensing element 134 may be resistance temperature detectors, thermistors or combinations thereof, which may be selected based on actual requirements. The thermistors in this case are semiconductors made of metal oxide and may be negative temperature coefficient (NTC) thermistors, or positive temperature coefficient (PTC) thermistors, while the resistance temperature detectors may be manufactured of metal, such as platinum, copper or nickel, but the disclosure is not limited thereto.

Continuously referring to FIG. 1, the liquid concentration detecting device 100 may further include a plurality of first electrical contacts 140 disposed on at least one of the third surface 116 and the fourth surface 118 of the second substrate 138 (which are illustrated as being respectively disposed on the third surface 116 and the fourth surface 118 in FIG. 1), and the heating element 132 and the second temperature sensing element 134 are electrically connected with different first electrical contacts 140 respectively. To be detailed, in the present embodiment, the first electrical contacts 140 (which are a pair of electrodes in this case) connected with the heating element 132 are located at the left side of the third surface 116 of the second substrate 138, and the other first electrical contacts 140 (which are another pair of electrodes) connected with the second temperature sensing element 134 are located at the right side of the fourth surface 118 of the second substrate 138. Namely, the first electrical contacts 140 respectively connected with the heating element 132 and with the second temperature sensing element 134 are two pairs of electrodes that are disposed on each side of the second substrate separately. In other words, the heating element 132 and the second temperature sensing element 134 are electrically disconnected from each other. In other embodiments, as long as the first electrical contacts 140 are not conducted with each other, the first electrical contacts 140 may be separately disposed on the same side or different sides on at least one of the third surface 116 and the fourth surface 118 of the second substrate 138, which are not limited in the disclosure. Additionally, the liquid concentration detecting device 100 further includes a second electrical contact 140' disposed on at least one of the first surface 112 and second surface 114 of the first substrate 110 (in the embodiment of FIG. 1, the second electrical contact 140' is disposed on the first surface 112), and the first temperature sensing element 120 is electrically connected with the second electrical contact 140'. In this case, the electrical connection between the elements and electrical contacts 140 and 140' may be achieved by means of wire bonding, direct stacking of printed solder joints or any other adaptive manners. The concentration sensor 130 and the first temperature sensing element 120 may be electrically connected to a signal processing center respectively through the electrical contacts 140 and 140'.

Description with respect to the detection performed by using the liquid concentration detecting device 100 will be set forth below.

Figure 2:
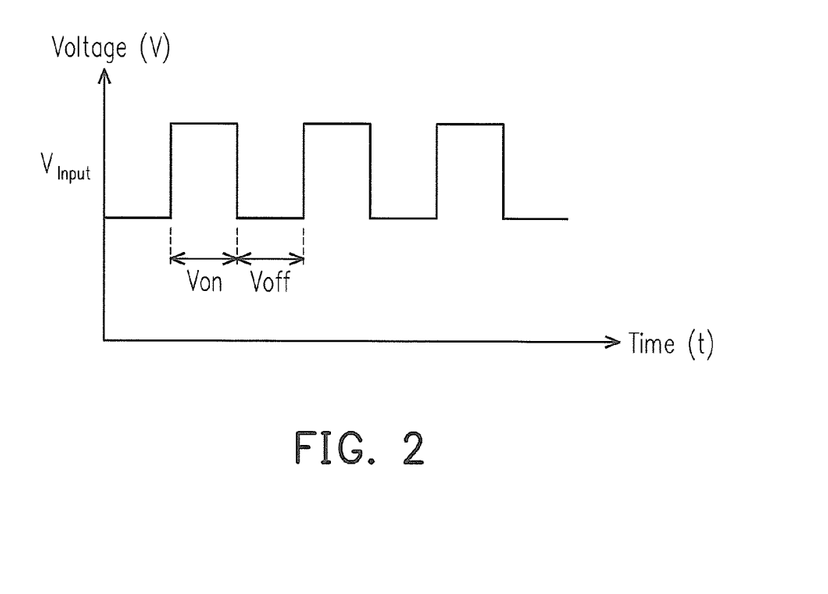
FIG. 2 is a relation graph illustrating an input voltage related with time.
Figure 3:
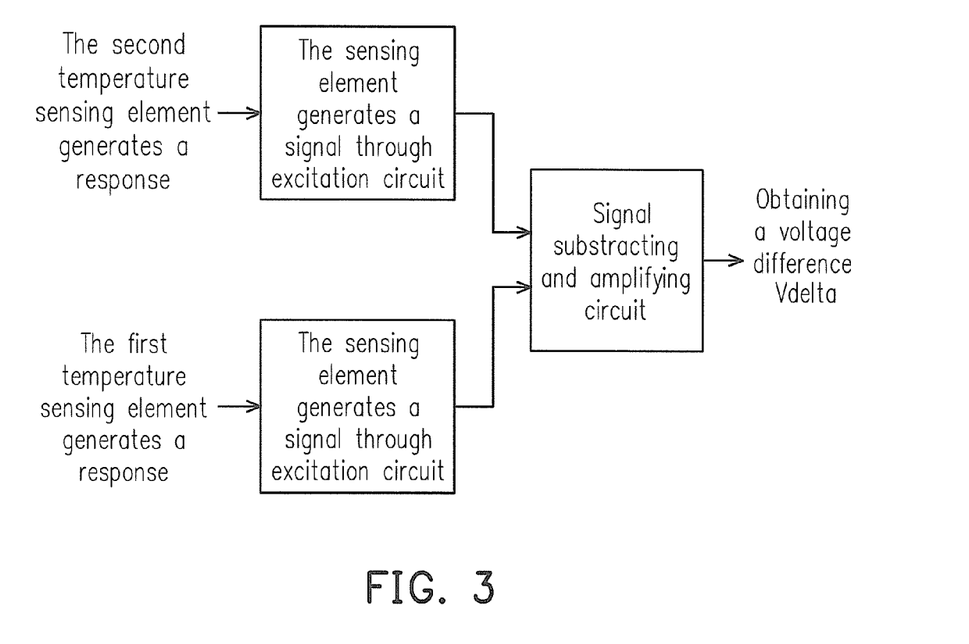
FIG. 3 is a schematic diagram illustrating a signal processing procedure.

FIG. 2 is a diagram illustrating the relation of an input voltage versus time. FIG. 3 is a schematic diagram illustrating a signal processing procedure. Referring to FIG. 1, FIG. 2 and FIG. 3, in this case, the liquid concentration detecting device 100 is placed in the liquid, and a portion of the liquid infiltrates into the porous element 136. Then, within a predetermined time period t, a predetermined pulse voltage is provided to serve as an input voltage $V_{Input}$ to the liquid concentration detecting device 100 for detecting the concentration of the liquid. Thus, when the liquid concentration detecting device 100 is placed in the liquid and applied with the input voltage $V_{Input}$, the heating element 132 of the concentration sensor 130 in the liquid concentration detecting device 100 heats up the portion of the liquid flowing into the porous element 136 during a voltage on time period Von, while the first temperature sensing element 120 measuring the temperature of the other portion of the liquid outside the porous element 136 generates a response (REF RTD INPUT) to generate a signal through the excitation circuit, and the second temperature sensing element 134 measuring the temperature of the portion of the liquid flowing into the porous element 136 generates another response (SENSOR RTD INPUT) to generate a signal. The signal processing center subtracts and amplifies the two signals to obtain a voltage difference Vdelta. In a voltage off time period Voff, the heating element 132 stops heating.

Figure 4:
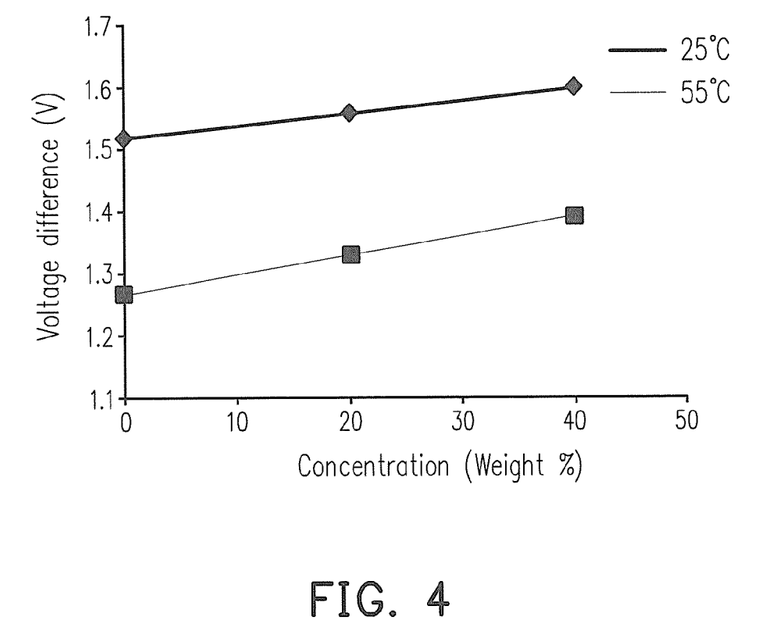
FIG. 4 is a relation graph of the liquid concentration detecting device output signals for liquids of different concentrations at different temperatures.
Figure 5:
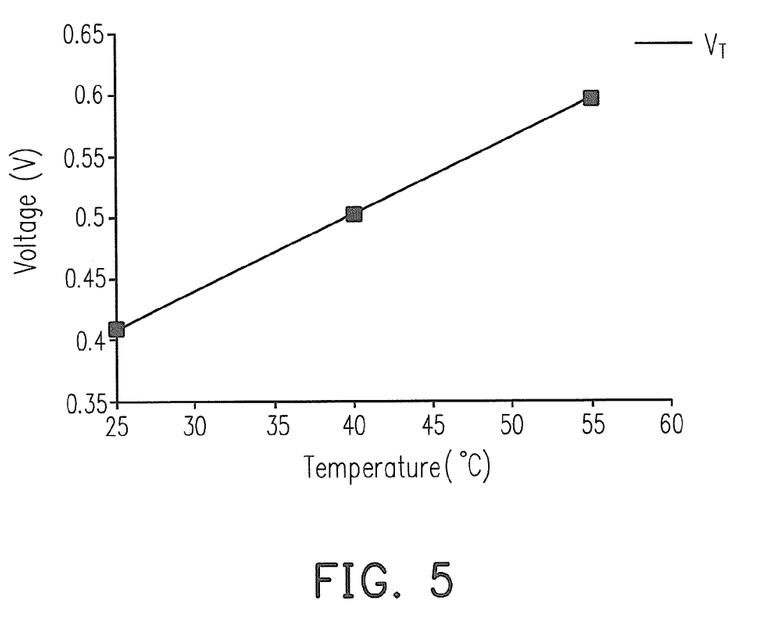
FIG. 5 is a relation graph illustrating the relation between an output signal of the first temperature sensing element and a temperature.

FIG. 4 is a diagram of the liquid concentration detecting device output signals for liquids of different concentrations at different temperatures, where the vertical axis represents the voltage difference Vdelta (unit: V), and the horizontal axis represents a liquid concentration Conc (unit: weight percentage (%)). According to FIG. 4, at different temperatures (e.g., 25° C. and 55° C.), the relation between the voltage difference and the liquid concentration is illustrated. FIG. 5 is a diagram illustrating the relation between the output signal of the first temperature sensing element and the temperature, where the voltage $V_T$ which represents the output signal of the first temperature sensing element versus the liquid temperature measured by the first temperature sensing element 120 shows a linear relationship between the voltage $V_T$ and the temperature. A selected input voltage $V_{Input}$ (e.g., the predetermined pulse voltage) is provided to heat up the liquid in the porous element 136 within the same predetermined time period t, and based on the specific heat principle (i.e., under the same calorie input, temperature rise varies with liquid concentration), the signal processing center transforms a solution concentration sensed by the liquid concentration detecting device 100 into a temperature variation which is then transformed into an output voltage difference by a temperature sensing resistor and a matching circuit and calculated according to calibration curves and data shown in FIG. 4 and FIG. 5 to deduce an accurate liquid concentration. It is to be additionally mentioned that the porous element 136 may also be made of a ceramic material with high thermal conductivity, so as to provide a good heat transfer path and achieve an effect of heating the liquid in the porous element 136.

It is to be additionally mentioned that when the liquid concentration is detected by using the liquid concentration detecting device 100, the porous element 136 has a plurality of holes penetrating through the surfaces, which may cause the liquid to infiltrate into the liquid concentration detecting device 100 for the detection by means of diffusion effect or capillary effect, and thus, bubbles may be prevented from entering the holes. Meanwhile, due to the multi-hole structure, the porous element 136 may provide a rough surface, such that the possibility of bubble attachment may be reduced to mitigate signal interference caused by the bubbles.

Furthermore, the porous element 136 may further control the amount of the liquid for heat exchange by adjusting the absorption thereof to amplify the detection signals. Alternatively, the porous element 136 may also control the heat exchange rate by adjusting the thickness thereof to improve overall detection sensitivity of the liquid concentration detecting device 100.

The afore-described liquid concentration detecting device 100 can achieve not only a capability of obtaining accurate detection results, but also a quick and uniform thermal conduction effect due to having a simple structure and each layer of the liquid concentration detecting device 100 (except for the first substrate 110 and the second substrate 138) capable of being manufactured by a printing process, which facilitates miniaturization of the liquid concentration detecting device 100. When being compared with other liquid concentration detecting device that requires a microelectromechanical (MEMS) thin film manufacturing process, the manufacturing cost of the liquid concentration detecting device 100 of the present embodiment may be effectively reduced.

Figure 6:
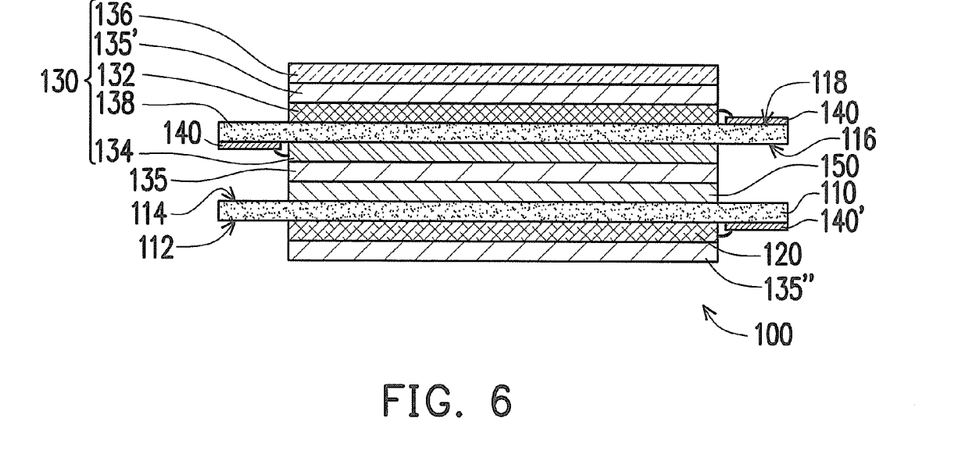
FIG. 6 is a schematic diagram illustrating another implementation aspect of the liquid concentration detecting device of the first embodiment of the disclosure.

In an alternative embodiment, positions of the heating element 132 and the second temperature sensing element 134 may be exchanged, i.e., the second temperature sensing element 134 is disposed between the second surface 114 of the first substrate 110 and the third surface 116 of the second substrate 138. In detail, the second temperature sensing element 134 is disposed on the third surface 116 of the second substrate 138 and located between the first sealing layer 135 and the second substrate 138, and the heating element 132 is located on the fourth surface 118 of the second substrate 138, and the porous element 136 is located on the heating element 132, as shown in FIG. 6.

[Second Embodiment]

Figure 7:
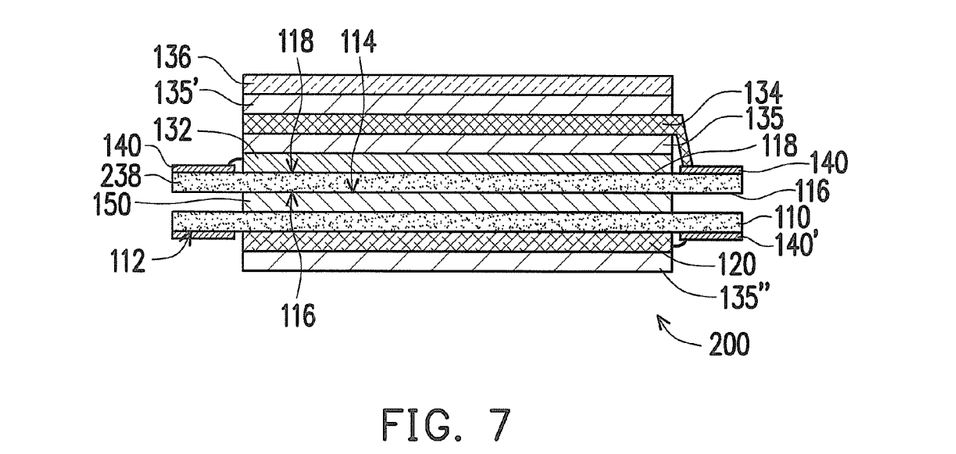
FIG. 7 is a schematic diagram illustrating a liquid concentration detecting device according to a second embodiment of the disclosure.

FIG. 7 is a schematic diagram illustrating a liquid concentration detecting device according to a second embodiment of the disclosure. In the present embodiment, a liquid concentration detecting device 200 has a structure and configuration similar to the structure and configuration of the liquid concentration detecting device 100 of the first embodiment, and thus, the reference numbers of elements of the first embodiment are referenced hereinafter. The present embodiment is different from the preceding embodiment in that both the second temperature sensing element 134 and the heating element 132 are located on the fourth surface 118 of the second substrate 238, and both the second temperature sensing element 134 and the heating element 132 are located between the second substrate 238 and the porous element 136. In detail, the second substrate 238 is located between the heating element 132 and the thermal insulation layer 150, and the first sealing layer 135 is disposed between the heating element 132 and the second temperature sensing element 134. The plurality of first electrical contacts 140 may be disposed on the same surface or different surfaces of the second substrate 238 based on actual requirements, and the heating element 132 and the second temperature sensing element 134 are electrically connected with their corresponding first electrical contacts 140 respectively. Therein, the manner in which the heating element 132 and the second temperature sensing element 134 are electrically connected with their corresponding first electrical contacts 140 respectively has been described in accordance with the first embodiment and thus, will not be repeated.

In comparison with the heating element 132 and the second temperature sensing element 134 located on opposite sides of the second substrate 138 in the first embodiment, the heating element 132 and the second temperature sensing element 134 of the present embodiment are located on the same side (i.e., on the fourth surface 118) of the second substrate 238 to meet variation in implementation according to different structural requirements. In the first embodiment, the second substrate 138 is disposed between the heating element 132 and the second temperature sensing element 134, so as to achieve the heating element 132 and the second temperature sensing element 134 being insulated from each other. Meanwhile, the second substrate 138 is considered as a good thermal conductor made of, for example, ceramic with the high thermal conductivity characteristic and thus, may transfer the heat from the heating element 132 through the second temperature sensing element 134 to heat the liquid in the porous element 136. Therein, the temperature measured by the second temperature sensing element 134 is the temperature of the heat generated by the heating element 132 and also the temperature of the heated liquid. In the present embodiment, the heating element 132 and the second temperature sensing element 134 are disposed on the same side (i.e., on the fourth surface 118) of the second substrate 238, and a thickness of the first sealing layer 135 may be designed as being smaller than a thickness of the second substrate 238, such that a heat transfer path from the heating element 132 through the first sealing layer 135 to the second temperature sensing element 134 is shorter than a heat transfer path from the heating element 132 through the second substrate 138 to the second temperature sensing element 134 in the first embodiment illustrated in FIG. 1, and may achieve a good liquid heating effect.

[Third Embodiment]

Figure 8:
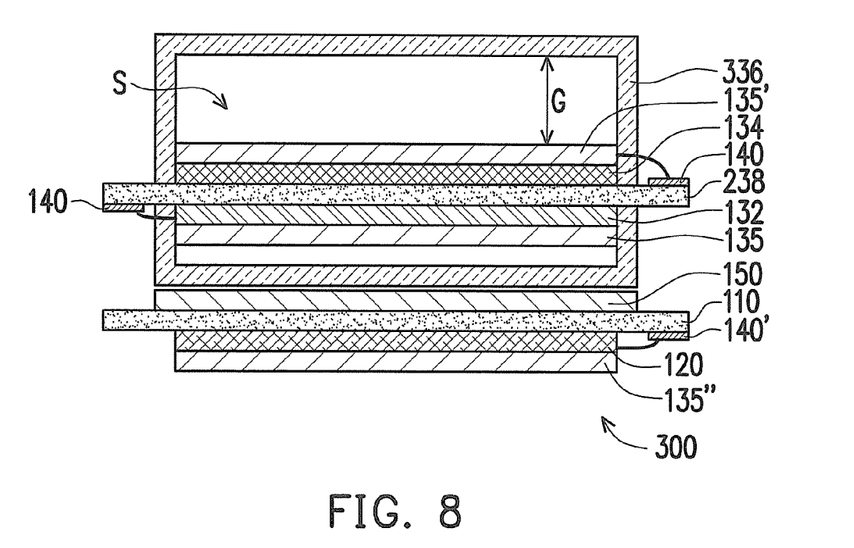
FIG. 8 is a schematic diagram illustrating a liquid concentration detecting device according to a third embodiment of the disclosure.

FIG. 8 is a schematic diagram illustrating a liquid concentration detecting device according to a third embodiment of the disclosure. In the present embodiment, a liquid concentration detecting device 300 has a structure and configuration similar to the structure and configuration of the liquid concentration detecting device 100 or 200 of the first embodiment or the second embodiment, and thus, the reference numbers of the elements of the first embodiment or the second embodiment are referenced hereinafter. The present embodiment is different from the preceding embodiments in that a porous element 336 of the present embodiment is cover-shaped and covers the second temperature sensing element 134 and the second sealing layer 135'. A gap G is between the porous element 336 and the second sealing layer 135' (or the second temperature sensing element 134) along a height direction of the liquid concentration detecting device 300. Namely, a chamber S is formed between the porous element 336 and the sealing layer 135' (or the second temperature sensing element 134).

With the cover-shaped porous element 336, the liquid under detection may be contained in the chamber S between the porous element 336 and the second sealing layer 135' and thereby, effect due to agitation from the liquid outside the porous element 336 may be mitigated.

[Fourth Embodiment]

Figure 9:
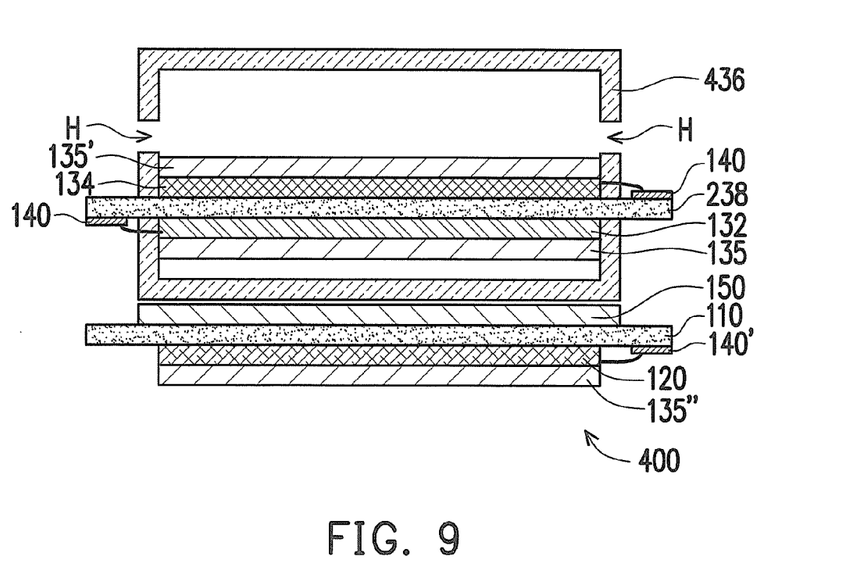
FIG. 9 is a schematic diagram illustrating a liquid concentration detecting device according to a fourth embodiment of the disclosure.

FIG. 9 is a schematic diagram illustrating a liquid concentration detecting device according to a fourth embodiment of the disclosure. In the present embodiment, a liquid concentration detecting device 400 has a structure and configuration similar to the structure and configuration of the liquid concentration detecting device 300 and thus, the reference numbers of elements of the third embodiment are referenced hereinafter. The present embodiment is different from the third embodiment in that the cover-shaped porous element 436 has a pair of openings H disposed opposite to each other, and the liquid may flow in and out of the openings H. The pair of openings H may be located at the same height or different heights, and in this case, FIG. 9 only illustrates that the openings are located at the same height.

The openings H may allow not only the liquid exchange through the penetrating holes of the cover-shaped porous element 436 by means of the diffusion effect or capillary effect, but also the liquid flowing in a faster speed by means of flowing through the openings H. Thus, during the voltage off time period Voff, the flowing liquid may facilitate the removal of excess heat accumulated on the second temperature sensing element 134.

Variations may be made to the combination of the porous elements 136, 336 or 436 of any one of the aforementioned embodiments with the second substrate, the heating element and the second temperature sensing element of the embodiments. To be more detailed, even the porous element 336 of the third embodiment may also be applied in the stacking structure of the second substrate 238, the heating element 132 and the second temperature sensing element 134 in the second embodiment, and the persons of the art can make choice and modification based on actual demands.

In light of the foregoing, the liquid concentration detecting device introduced by the disclosure at least achieves the following:

1. the elements may be printed and formed on the substrates, of which the cost can be effectively controlled;
2. the structure is simple and not only miniaturization of the overall dimension but also a quick and uniform thermal conduction effect can be achieved, which can facilitate obtaining accurate measurement results;
3. the porous element can prevent the entering of bubbles and reduce the possibility of bubble attachment due to surface roughness, so as to mitigate signal interference incurred by the bubbles;
4. controlling the liquid amount for heat exchange to enlarge the sensed signal can be achieved by means of adjusting the absorption of the porous element or the size of the chamber of the cover-shaped porous element, or alternatively, controlling the heat exchange rate can be achieved by means of adjusting the thickness of the porous element or the sizes of the openings of the cover shape porous element, so as to improve the overall detection sensitivity of the liquid concentration detecting device; and
5. the liquid concentration detecting device can achieve a variety of implementations which can be selected according to different demands to obtain accurate detection results that meets the demands.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A liquid concentration detecting device, adapted for detecting a concentration of a liquid, comprising:
   a first substrate, having a first surface and a second surface opposite to each other;

a first temperature sensing element, disposed on the first surface and sensing a temperature of the liquid in the external of the liquid concentration detecting device;

a concentration sensor, disposed on the second surface, comprising:
  a second substrate, disposed on the second surface, having a third surface and a fourth surface opposite to each other, wherein the third surface faces the second surface;
  a porous element, located above the fourth surface of the second substrate, wherein a portion of the liquid flows into the concentration sensor through the porous element;
  a heating element, heating the portion of the liquid flowing into the concentration sensor; and
  a second temperature sensing element, sensing a temperature variation of the portion of the liquid flowing into the concentration sensor, wherein the measured temperature and temperature variation are compared to extrapolate the concentration of the liquid under detection.

2. The liquid concentration detecting device according to claim 1, wherein the heating element is disposed between the second surface of the first substrate and the third surface of the second substrate, the second temperature sensing element is located on the fourth surface of the second substrate, and the porous element is located on the second temperature sensing element.

3. The liquid concentration detecting device according to claim 1, wherein the second temperature sensing element is disposed between the second surface of the first substrate and the third surface of the second substrate, the heating element is located on the fourth surface of the second substrate, and the porous element is located on the heating element.

4. The liquid concentration detecting device according to claim 1, wherein both the second temperature sensing element and the heating element are located on the fourth surface of the second substrate, and both the second temperature sensing element and the heating element are disposed between the second substrate and the porous element.

5. The liquid concentration detecting device according to claim 1, further comprising:
  a first sealing layer, disposed between the concentration sensor and the first substrate.

6. The liquid concentration detecting device according to claim 1, further comprising:
  a first sealing layer, disposed between the heating element and the second temperature sensing element.

7. The liquid concentration detecting device according to claim 1, further comprising:
  a second sealing layer, disposed between the second temperature sensing element and the porous element.

8. The liquid concentration detecting device according to claim 1, further comprising:
  a third sealing layer, disposed on a surface of the first temperature sensing element which is away from the first surface of the first substrate.

9. The liquid concentration detecting device according to claim 1, wherein the porous element is a single-layer structure.

10. The liquid concentration detecting device according to claim 1, wherein an absorption of the porous element is greater than 15%.

11. The liquid concentration detecting device according to claim 1, wherein a material of the porous element is ceramic.

12. The liquid concentration detecting device according to claim 1, wherein at least one of the first substrate and the second substrate is a ceramic substrate.

13. The liquid concentration detecting device according to claim 1, wherein thermal conductivity coefficients of the first substrate and the second substrate are greater than 20W/M*K.

14. The liquid concentration detecting device according to claim 1, wherein the first temperature sensing element and the second temperature sensing element are resistance temperature detectors, thermistors or combinations thereof.

15. The liquid concentration detecting device according to claim 1, further comprising:
  a plurality of first electrical contacts, disposed on at least one of the third surface and the fourth surface of the second substrate, and the heating element and the second temperature sensing element are electrically connected with the different first electrical contacts respectively.

16. The liquid concentration detecting device according to claim 1, further comprising:
  a second electrical contact, disposed on at least one of the first surface and the second surface of the first substrate, and the first temperature sensing element is electrically connected with the second electrical contact.

17. The liquid concentration detecting device according to claim 1, further comprising:
  a thermal insulation layer, disposed between the first substrate and the heating element.

18. The liquid concentration detecting device according to claim 1, wherein the porous element is cover-shaped and covers the second temperature sensing element.

19. The liquid concentration detecting device according to claim 18, wherein a gap is between the porous element and the second temperature sensing element along a height direction of the liquid concentration detecting device.

20. The liquid concentration detecting device according to claim 19, wherein the porous element has a pair of openings disposed opposite to each other, and the liquid is adapted to flow in and out through the openings.

* * * * *

UNITED STATES PATENT AND TRADEMARK OFFICE
CERTIFICATE OF CORRECTION

PATENT NO. : 9,766,193 B2  
APPLICATION NO. : 14/583212  
DATED : September 19, 2017  
INVENTOR(S) : Tzu-Yu Liu et al.

Page 1 of 1

It is certified that error appears in the above-identified patent and that said Letters Patent is hereby corrected as shown below:

On the Title Page (71) Applicants should read: Industrial Technology Research Institute, Hsinchu (TW); QIAN JUN TECHNOLOGY LTD., New Taipei City (TW)

Signed and Sealed this
Nineteenth Day of December, 2017

Joseph Matal
*Performing the Functions and Duties of the*
*Under Secretary of Commerce for Intellectual Property and*
*Director of the United States Patent and Trademark Office*